(12) United States Patent
Foster

(10) Patent No.: US 9,550,058 B2
(45) Date of Patent: Jan. 24, 2017

(54) COMPOUND-SHAPED STYLET FOR TORQUE TRANSMISSION

(71) Applicant: Cardiac Pacemakers, Inc., St. Paul, MN (US)

(72) Inventor: Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 637 days.

(21) Appl. No.: 13/846,440

(22) Filed: Mar. 18, 2013

(65) Prior Publication Data

US 2014/0058405 A1 Feb. 27, 2014

Related U.S. Application Data

(60) Provisional application No. 61/693,418, filed on Aug. 27, 2012.

(51) Int. Cl.
| | | |
|---|---|---|
| *A61N 1/05* | (2006.01) | |
| *A61N 1/36* | (2006.01) | |
| *A61N 1/362* | (2006.01) | |

(52) U.S. Cl.
CPC ............ *A61N 1/0592* (2013.01); *A61N 1/056* (2013.01); *A61N 1/0551* (2013.01); *A61N 1/362* (2013.01);
(Continued)

(58) Field of Classification Search
CPC ...... A61N 1/0592; A61N 1/059; A61N 1/362; A61N 1/0573; A61N 1/36017; A61N 1/056; A61N 1/0558; A61N 1/0563; A61N 1/05; A61N 1/0565; A61N 1/057; A61N 1/3956; A61B 18/1492; A61B 18/14; A61B 18/1477; A61B 10/0233; A61B 17/3421; A61B 17/3417; A61B 17/320758; A61B 2010/0208; A61B 2018/00273; A61B 2018/1425; A61B 1/0051; A61B 2017/3454; A61B 5/6852; A61M 25/0102; A61M 25/0606; A61M 25/0032; A61M 25/0043; A61M 25/01; A61M 25/0194

See application file for complete search history.

(56) References Cited

U.S. PATENT DOCUMENTS

| | | |
|---|---|---|
| 4,046,151 A | 9/1977 | Rose |
| 4,136,701 A | 1/1979 | Barton et al. |

(Continued)

OTHER PUBLICATIONS

International Search Report and Written Opinion issued in PCT/US2013/032842, mailed Aug. 12, 2013, 10 pages.
(Continued)

*Primary Examiner* — Jocelin Tanner
(74) *Attorney, Agent, or Firm* — Faegre Baker Daniels LLP

(57) ABSTRACT

A medical stylet for guiding a lead includes a first elongate member for attachment of the lead to the target tissue, a second elongate member to reshape the lead. The first elongate member of the medical stylet includes a proximal end portion, and a distal end portion wherein the distal end portion of the first elongate member includes a tip feature configured to engage the lead on application of torque externally. The second elongate member defines a lumen along its length. The lumen of the second elongate member can be configured to enclose at least a portion of the first elongate member. The second elongate member can have a pre defined shape. The pre defined shape of the second elongate member allows the lead to be reshaped when inserted into the lead, this reshaped lead now can be guided to an anatomical pass way.

18 Claims, 7 Drawing Sheets

(52) U.S. Cl.
CPC ........ *A61N 1/3605* (2013.01); *A61N 2001/058* (2013.01)

(56) References Cited

U.S. PATENT DOCUMENTS

| | | | |
|---|---|---|---|
| 4,136,703 A | | 1/1979 | Wittkampf |
| 4,209,019 A | * | 6/1980 | Dutcher et al. ............... 607/127 |
| 4,215,703 A | | 8/1980 | Willson |
| 4,257,428 A | * | 3/1981 | Barton et al. ................. 607/128 |
| 4,350,169 A | * | 9/1982 | Dutcher et al. ............... 607/119 |
| 4,357,946 A | * | 11/1982 | Dutcher ............... A61N 1/0587 607/131 |
| 4,381,013 A | * | 4/1983 | Dutcher ................ A61N 1/056 607/127 |
| 4,458,677 A | * | 7/1984 | McCorkle, Jr. ........ A61N 1/056 607/123 |
| 4,479,500 A | * | 10/1984 | Smits ........................... 607/123 |
| 4,924,881 A | | 5/1990 | Brewer |
| 5,056,516 A | | 10/1991 | Spehr |
| 5,662,119 A | | 9/1997 | Brennen et al. |
| 5,697,936 A | | 12/1997 | Sbipko et al. |
| 7,280,876 B1 | * | 10/2007 | Tockman ............... A61N 1/056 607/125 |
| 2001/0007071 A1 | * | 7/2001 | Koblish ............. A61B 18/1492 606/41 |
| 2002/0161423 A1 | | 10/2002 | Lokhoff et al. |
| 2003/0167082 A1 | * | 9/2003 | Ollivier ................ A61N 1/0573 607/126 |
| 2009/0054963 A1 | | 2/2009 | Osypka |
| 2011/0009878 A1 | | 1/2011 | Haldeman et al. |
| 2011/0112619 A1 | | 5/2011 | Foster et al. |
| 2012/0035616 A1 | | 2/2012 | Olsen et al. |
| 2012/0191169 A1 | | 7/2012 | Rothstein et al. |

OTHER PUBLICATIONS

International Preliminary Report on Patentability issued in PCT/US2013/032842, completed Mar. 3, 2015, 10 pages.

* cited by examiner

COMPOUND-SHAPED STYLET FOR TORQUE TRANSMISSION

CROSS-REFERENCE TO RELATED APPLICATION

This application claims priority to U.S. Provisional Application No. 61/693,418, filed Aug. 27, 2012, which is herein incorporated by reference in its entirety.

TECHNICAL FIELD

The present disclosure relates to a medical stylet. More specifically, the invention relates to a pre-shaped stylet for implanting a lead in the heart of a patient and for delivering torque to a distal lead feature.

BACKGROUND

Implantable medical leads can be used to deliver electrical stimulation to the body tissue through implantable medical devices. Exemplary implantable devices include cardiac rhythm management (CRM) systems (e.g., pacemakers, defibrillators, and cardiac resynchronization therapy devices) and neurostimulation systems (e.g., spinal cord stimulation (SCS) systems). For CRM systems, the medical leads typically extend intravascularly to an implant location within or on a patient's heart. The implantable medical leads can be equipped with at least one electrode. The implantable medical leads are often positioned so that the electrode delivers electrical stimulation to a target tissue without stimulating adjacent tissue. The implantable medical leads can be flexible and can require use of a support device (e.g., a stylet) to effectively guide the implantable medical lead into a desired location inside the heart of a patient. A stylet-driven implantable medical lead can have a preformed shape to facilitate advancement of the medical lead to certain locations within the heart.

Implantable medical leads are often anchored or fixed to heart tissue using an active (i.e., movable or deployable) fixation anchor, such as a rotatable helix, located at or near a distal end of the lead. As the medical leads are typically flexible in torsion, it can be a challenge to use the lead body to rotate the helix. For stylet-driven implantable medical leads, the stylet can operate to deliver torque from a proximal end of the lead to an active fixation mechanism at or near the distal end of the lead.

SUMMARY

Example 1 is a medical stylet for use in delivering and anchoring an implantable medical lead to a desired location near or in a patient's heart. The stylet includes an inner member, having a distal end portion and a proximal end portion, wherein the distal end portion includes a tip feature configured to rotationally engage a coupling feature at or near a distal end of the implantable medical lead. The coupling feature is rotationally coupled to an anchoring mechanism including a fixation feature. The stylet further includes an outer member defining a lumen along its length, the lumen configured to accept and allow rotation of at least a portion of inner member. The outer member has a predetermined shape and sufficient stiffness to impart the shape upon the lead. The shape is selected to assist in delivery of the lead to the desired implant location. The inner member has sufficient torsional stiffness to transmit a torque from the proximal end portion to the coupling feature, so as to rotate the anchoring mechanism.

Example 2 is the medical stylet of Example 1, further comprising an actuating mechanism and wherein the proximal end portion of the inner member is configured to be rotated by the actuating mechanism.

Example 3 is the medical stylet of Example 1 or 2, wherein the tip feature is configured to be manipulated by the actuating mechanism to engage with the coupling feature of the implantable medical lead.

Example 4 is the medical stylet of any of Examples 1-3, wherein the inner member is made from at least one of steel, titanium, nickel, and a polymer.

Example 5 is the medical stylet of any of Examples 1-4, wherein the tip feature of the inner member defines a non-circular shape.

Example 6 is the medical stylet of any of Examples 1-5, wherein the predetermined shape of the outer member is a J-shape and the desired location in an atrium of the heart.

Example 7 is the medical stylet of any of Examples 1-6, wherein the predetermined shape of the outer member is an L-shape and the desired location is a His bundle of the heart.

Example 8 is the medical stylet of any of Examples 1-7, wherein the predetermined shape is a multi-planar shape.

Example 9 is the medical stylet of any of Examples 1-8, wherein the outer member is made from at least one of a stainless steel and a nickel-cobalt alloy.

Example 10 is the medical stylet of any of Examples 1-9, wherein the inner member has a torsional stiffness sufficient to deliver a torque to the coupling feature, with less than 360 degrees rotation along its length, in an amount between about 20 and about 100 micronewton-meters.

Example 11 is a cardiac lead assembly including an implantable medical lead having a lead body having a lead proximal end and a lead distal end and a lead lumen extending therethrough. The lead further including an anchoring mechanism disposed at or near the lead distal end, the anchoring mechanism having a coupling feature and a fixation feature. The assembly includes a stylet for use in guiding the implantable lead to a desired implant site. The stylet includes an inner member, having a distal end portion and a proximal end portion, wherein the distal end portion includes a tip feature. The tip feature is configured to rotationally engage the coupling feature at or near the distal end of the implantable medical lead. The stylet further includes an outer member defining a stylet lumen along its length, the stylet lumen configured to accept and allow rotation of at least a portion of inner member. The outer member has a predetermined shape and sufficient stiffness to at least partially impart the shape upon the lead. The shape is selected to assist in delivery of the desired implant site. The inner member has sufficient torsional stiffness to transmit a torque from the proximal end portion to the coupling feature, so as to rotate the anchoring mechanism.

Example 12 is the cardiac lead assembly of Example 11, wherein the inner member is made from at least one of steel, titanium, nickel, and a polymer.

Example 13 is the cardiac lead assembly of Example 11 or 12, wherein the tip feature of the inner member defines a non-circular shape.

Example 14 is the cardiac lead assembly of any of Examples 11-13, wherein the anchoring mechanism includes a helix configured for engaging and anchoring with tissue in or near a patient's heart.

Example 15 is the cardiac lead assembly of any of Examples 11-14, wherein the predetermined shape is a multi-planar shape.

Example 16 is the cardiac lead assembly of any of Examples 11-15, wherein the outer member is made from at least one of a stainless steel and a nickel-cobalt alloy.

Example 17 is the cardiac lead assembly of any of Examples 11-16, wherein the inner member has a torsional stiffness sufficient to deliver a torque to the coupling feature, with less than 360 degrees rotation along its length, in an amount between about 20 and about 100 micronewton-meters.

Example 18 is the cardiac lead assembly of any of Examples 11-17, wherein the fixation feature is a fixation helix.

Example 19 is a method of placing a lead in an anatomical location, using a medical stylet. The method includes inserting the medical stylet into a lumen defined by the lead, the medical stylet including an inner member, and an outer member at least partially surrounding the inner member, the outer member configured for providing a shape to the lead in accordance with an anatomical passageway, wherein the lead includes an anchoring mechanism having a coupling feature. The method further includes guiding the stylet along the anatomical passageway to the anatomical location. The method further includes rotating the medical stylet so as to cause the inner member to impart torque upon the coupling feature thereby causing the anchoring mechanism to rotate and engage tissue to anchor the lead at the anatomical location.

Example 20 is the method of Example 19, further comprising retracting the medical stylet after anchoring the lead at the anatomical location.

While multiple embodiments are disclosed, still other embodiments of the present disclosure will become apparent to those skilled in the art from the following detailed description, which describes and depicts illustrative embodiments of the invention. Accordingly, the drawings and detailed description are to be regarded as illustrative in nature and not restrictive.

Figure 1:
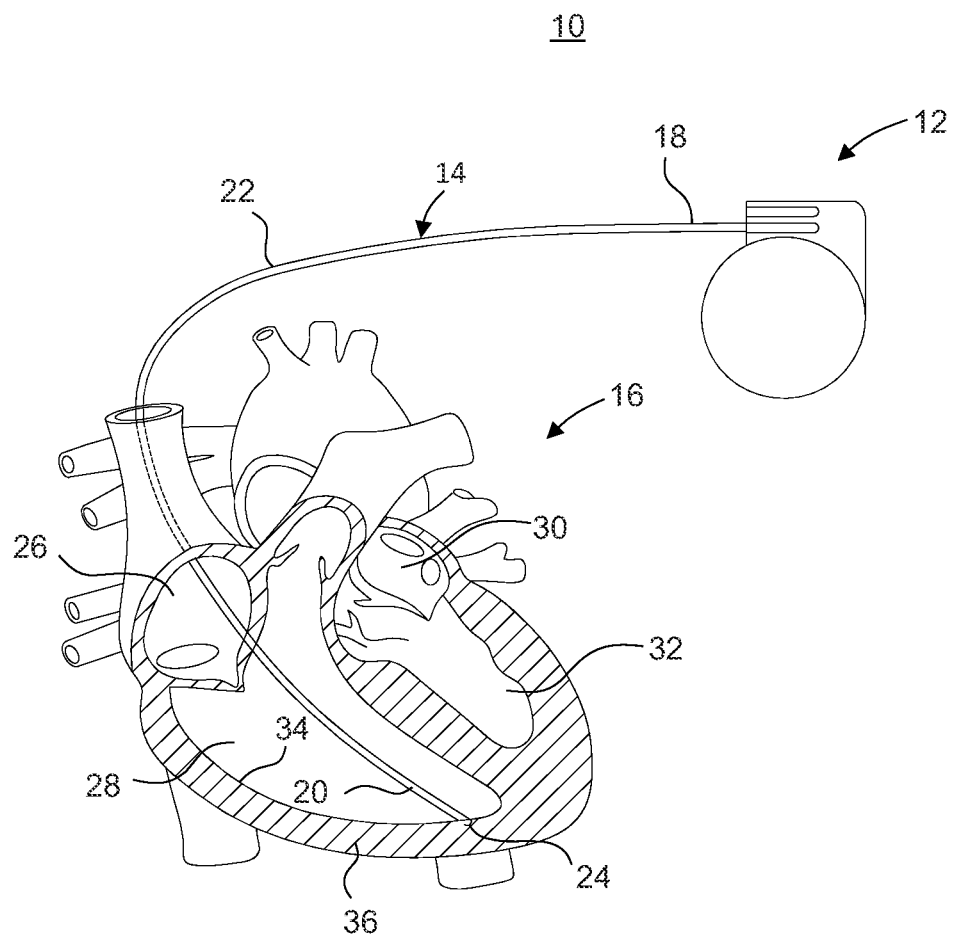
FIG. 1 is a perspective view of an implantable medical device in a cardiac rhythm management (CRM) system, according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. As shown, the system 10 includes an implantable rhythm management device 12 and an implantable lead 14, which extends from a proximal end portion 18 to a distal end portion 20. As shown in FIG. 1, the heart 16 includes a right atrium 26, a right ventricle 28, a left atrium 30, and a left ventricle 32. As further shown, the heart 16 includes an endocardium 34 covering the myocardium 36. As shown, an anchoring mechanism (e.g., a fixation helix) 24 located at the distal end portion 20 of the lead 14 penetrates through the endocardium 34 and is embedded in the myocardium 36. In some embodiments, the anchoring mechanism 24 is electrically active and thus, operates as a helical electrode for sensing the electrical activity of the heart 16 and/or applying a stimulating pulse to the right ventricle 28. In various embodiments, the anchoring mechanism 24 includes a coupling feature for coupling with a stylet and a fixation feature for engaging and anchoring with tissue in or near the heart 16. In various embodiments, the CRM system 10 includes a plurality of leads similar to the lead 14. For example, it can include a first lead that can be similar to the lead 14 adapted to convey electrical signals between the pulse generator (which can be the implantable rhythm management device) 12 and the right ventricle 28 and a second lead (not shown) adapted to convey electrical signals between the pulse generator 12 and the right atrium 26 or coronary veins (not shown).

Figure 2A:
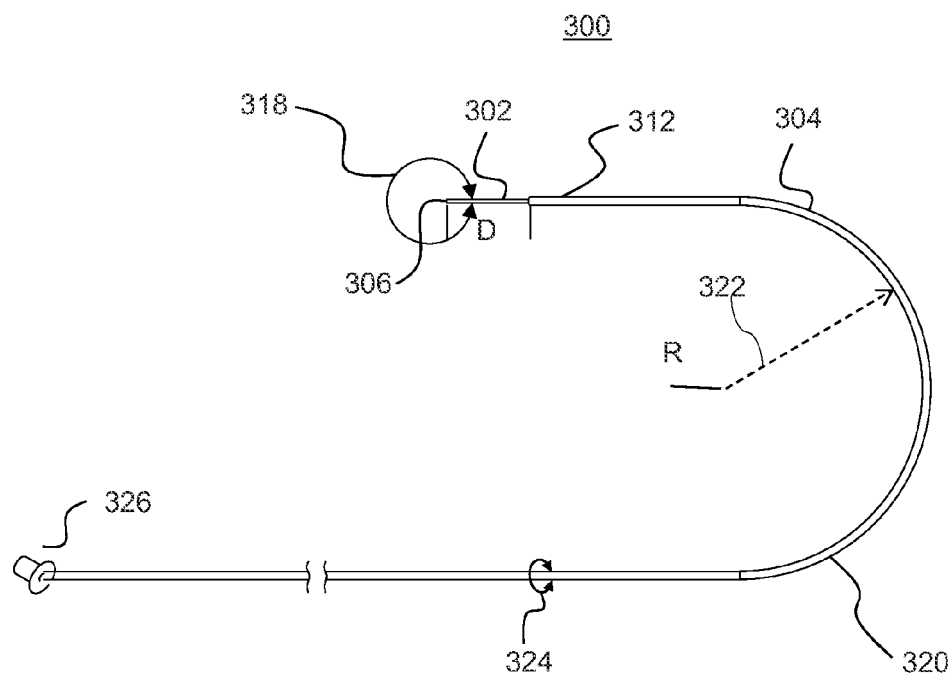
FIGS. 2A-2C show views of a medical stylet, according to various embodiments.
Figure 2B:
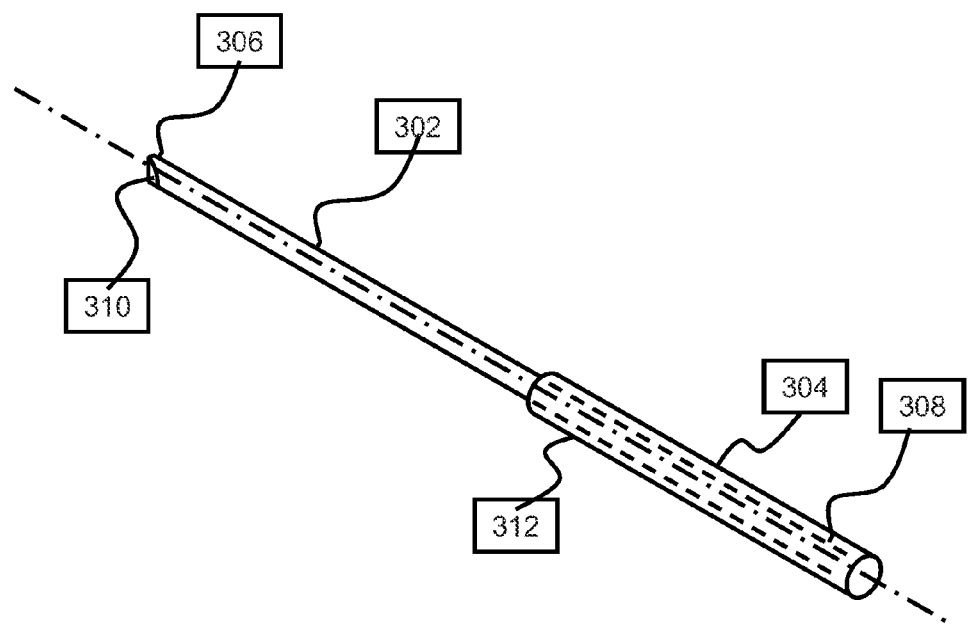
Figure 2C:
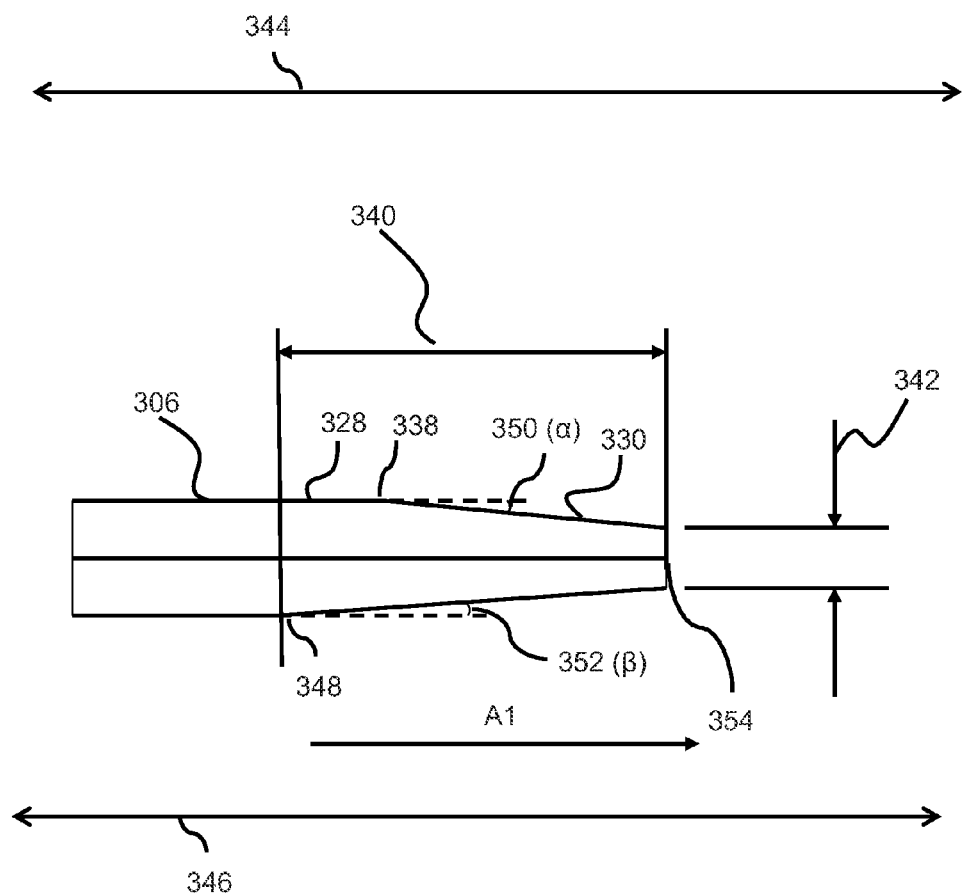

FIGS. 2A-2C show various view and portions of a stylet 300 for assisting with delivery of the lead 14 to a desired location within or near the patient's heart. As shown in FIG. 2A, the stylet 300 includes an inner elongate member 302, an outer elongate member 304, and an actuating mechanism 326. The inner member 302 and outer member 304 are sized and shaped such that the inner member 302 can be disposed within the outer member 304, in such a manner that the inner member 302 can be translated and rotated within the outer member 304. This translation and rotation can be accomplished by the actuating mechanism 326 in various embodiments. In other embodiments, the stylet 300 does not include an actuation mechanism 326. In these embodiments, this translation and rotation can be accomplished directly by a user (e.g., a physician) manipulating one or both of the inner member 302 and the outer member 304.

As further shown in FIG. 2A, the stylet 300 has a length defined by the length of the inner member 302, which has a length greater than a corresponding length of the outer member 304. As shown, the length of the inner member 302 exceeds the length of the outer member 304 by a distance "D." The inner member 302 includes a distal tip portion 306, which extends beyond a distal portion 312 of the outer member 304. In exemplary embodiments, the length of the medical stylet 300 is selected based on a corresponding length of the lead 14 that the stylet will be used to help implant. For example, the stylet 300 can have a sufficient length to extend from proximal to a lead proximal end to a location at or near a distal end of the lead. In various embodiments, the length of the stylet 300 is between about 400 mm and about 600 mm. More specifically, in certain embodiments, the length of the stylet 300 is one of 450 mm, 520 mm, 580 mm, and 590 mm. In various embodiments, the distance "D" is between about 1 mm and about 20 mm. According to various embodiments, the inner member 302 has an outer diameter of between about 0.0040 inches and 0.0100 inches, and the outer member 304 has an outer diameter of between about 0.0050 inches and about 0.0250 inches. In some embodiments, the outer diameter of the inner member 302 is 0.0080 inches, and the outer diameter of the outer member 304 is 0.017 inches.

In some embodiments, the implantable lead 14 including a silicone lead body, which is generally flexible and not configured to have a predetermined shape. The implantable lead 14 can be configured for placement in a variety of locations in or near the heart 16, including the atrial wall, the ventricular wall, the septal wall, or a location at or near the bundle of His (located at or near the atrioventricular node). To assist in delivering the implantable lead 14 through the patient's vascular system and to a desired location in or near the heart (such as those described above), it is helpful to have a mechanism to impart a desired shape or curvature upon the lead body. As the lead body is often made from a soft, silicone material, one such mechanism is through the use of a stylet 300 having a preset or predetermined shape. Upon placing such a stylet within a lumen of the implantable lead, the lead will conform to the shape of the stylet 300. As shown in FIG. 2A, for example, the stylet 300 is preformed, as further explained below, with a curved distal portion 320 having a radius of curvature 322.

The outer member 304 includes an inner lumen extending along its length. The lumen is sized to accept the inner member 302 to form the stylet 300. In various embodiments, the outer member 304 of the medical stylet 300 is formed of sufficiently stiff material to allow the outer member 304 to hold a predetermined shape. In various embodiments, the outer member 304 is made from one or more of a steel, steel alloy (including, for example, stainless steel) titanium, titanium alloys, nickel, nickel alloy, nickel-titanium alloy (including, for example, Nitinol and MP35N), or a polymer (e.g., PEEK or polyamide). In some embodiments, the outer member 304 is made from a stainless steel or a nickel cobalt alloy. In various embodiments, the second elongate member 304 is configured to have a predefined J-shape, wherein the J-shape is selected to allow the lead 14 to be placed at a desired location in or near the heart 16. As shown in FIG. 3B, the outer member 304 has a distal curved portion having a radius of curvature 322 of between about 0.40 and 0.50 inches. This radius of curvature can be selected to direct a distal portion of the implantable lead 14 to a desired location in the atrium. In other embodiments, the curved portion is configured with a predetermined wider curve, or with an L-shape, for example to assist in directing a distal portion of the implantable lead to a location near the bundle of His.

As shown in FIGS. 2B-2C, the inner member 302 of the stylet 300 includes a distal tip portion 306, which is configured to engage with a portion of the implantable lead 14. By engaging appropriately with a distal portion of the implantable lead, the stylet can operate to transmit a torque from a proximal end of the stylet to a component of the implantable lead. In some embodiments, the inner member 302 can be configured to be substantially straight along its length and to have a substantially circular cross-section. The substantially straight shape of the first elongate member 302 facilitates delivery of torque along its length and ultimately to a component of the lead 14 to which it is rotationally coupled. The inner member 302 is made of a material having torsional stiffness. According to various embodiments, the inner member 302 is made from one or more of a steel, steel alloy (including, for example, stainless steel) titanium, titanium alloys, nickel, nickel alloy, nickel-titanium alloy (including, for example, Nitinol and MP35N), or a polymer (e.g., PEEK or polyamide). In some embodiments, the distal tip portion 306 of the inner member 302 is formed of a polymer and the remaining length is formed of stainless steel or Nitinol. In other embodiments, the distal tip portion 306 is formed of a metal and the remaining length of the inner member 302 is formed of a polymer. The inner member 302 may be formed as a tube, a wire, a cable, a coil, or any combination of these elements.

FIG. 2B is a perspective view of the tip portion 306 of the inner member 302 extending from the proximal portion 312 of the second elongate member 304. As shown, the tip portion 306 includes a tip feature 310. This feature 310 can function to both facilitate engagement with a corresponding lead feature and to transfer torque from the inner member 302 to a corresponding lead feature. The tip feature 310 can be any shape capable of engaging with a corresponding shape on a lead feature, including, for example, a flat face, a triangular sectional shape, a square sectional shape, a star sectional shape, a hex sectional shape, a star shape (e.g., a Torx® profile), or other custom shape capable of transferring torque. The specific dimensions of the feature 310 are selected to provide a close (e.g., interference) fit with a corresponding feature on the component of the lead 14.

FIG. 2C shows an exemplary tip portion 306 of the inner member 302 of the medical stylet 300. As shown, the tip portion 306 includes a proximal portion 328 and a distal portion 330. The tip portion 306 can include a length 340 extending from the proximal portion 328 to the distal portion 330. The length 340 can vary from 0.04 inch to 0.08 inch. In some embodiments, the length 340 can be 0.06 inch. The tip portion 306 can be configured to include a first swage point 338 along a plane 344. The first swage point 338 can be defined and configured so that the proximal portion 328 forms a first swage angle 350 ($\alpha$) with the distal portion 330. The first swage point 338 can be the point where the proximal portion 328 meets the distal portion 330. The proximal portion 328 can be configured to be substantially straight. The tip portion 306 can be configured to define a second swage point 348 along a plane 346. The second swage point 348 can be defined and configured so that the proximal portion 328 forms a second swage angle 352 ($\beta$) with the distal portion 330. The second swage point 348 can define the point where the tip portion 306 meets other components of the first elongate member 302.

In various embodiments, the tip portion 306 can be configured so that the first swage angle 350 ($\alpha$) can be substantially opposite to the second swage angle 352 ($\beta$). The first swage point 338, the first swage angle 350 ($\alpha$), the second swage point 348, or the second swage angle 352 ($\beta$) can be positioned or configured so as to allow various shapes to be designed for the tip portion 306 such as to facilitate fixation of the tip portion 306 to the coupler 356 of the lead 14 for lead torque delivery or lead implantation. In an embodiment, the tip feature 310 can be configured to have one of bladed, triangular cut, square cut, Philips, Torx®, hex, or any other custom keyed head for easy fixation with the coupler 356 placed inside the lead 14. The distal portion 330 of the tip portion 306 can be configured to define a width 342. The width 342 can be configured so that it decreases along the direction A1 starting from the first swage point 338 or the second swage point 348, and extending until an end point 354 located on the distal portion 330. In an embodiment, the width 342 can vary between 0.005 inch and 0.009 inch. In an embodiment, the width 342 can be 0.007 inches at end point 354.

Figure 3A:
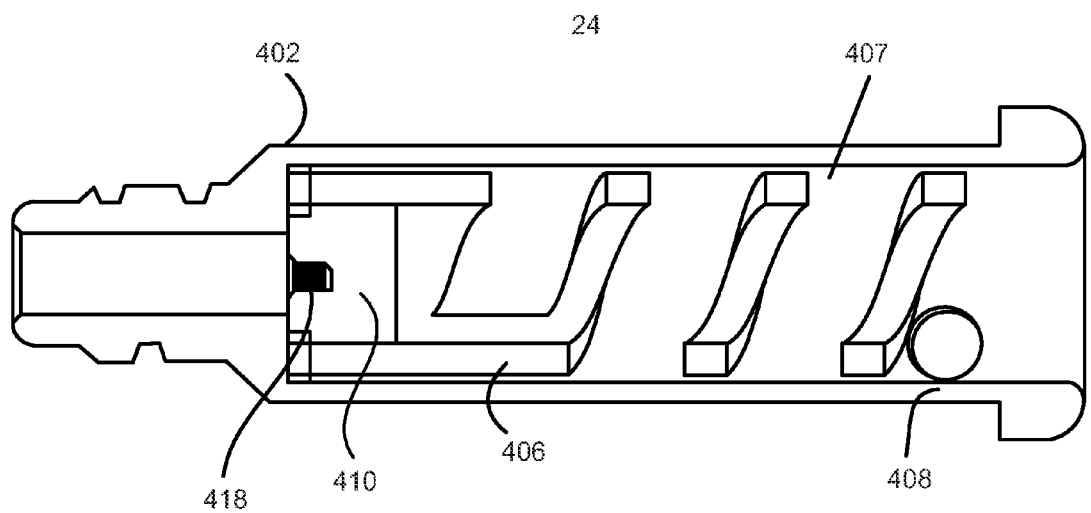
FIG. 3A is a schematic diagram illustrating a distal portion of an implantable medical lead.
Figure 3B:
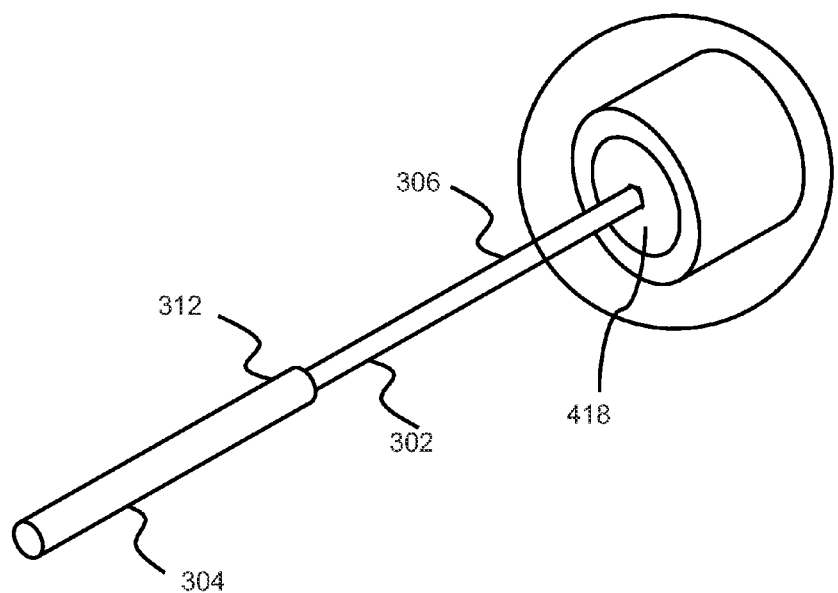
FIG. 3B is a schematic diagram illustrating a medical stylet engagement to a coupler of a lead.

FIG. 3A is a sectional view of components of an anchoring mechanism (e.g., a fixation helix) 24 of an implantable medical lead 14. As described above, the anchoring mechanism 24 is typically coupled at or near a distal end of the medical lead 14, and it operates to help anchor or secure the lead 14 at a desired location in or near the patient's heart. As shown, the anchoring mechanism 24 includes a housing 402 and a rotatable helical member (i.e., fixation feature) 406. The housing 402 and helical member 406 are configured such that upon rotation of the helical member, it will advance forward such that it extends from a distal end or the housing 402. In this way, the helical member 406 may extend into and engage tissue to perform an anchoring function. In some embodiments, the housing 402 is active such that it operates as an electrode. In some embodiments, an internal surface of the housing 402 is lined with a polymer liner 407 to prevent electrical communication between the housing and the helical member. In some embodiments, the housing 402 further includes a peg, which holds the helical member 406 in place and allows the helical member 406 to extend from the housing 402 only upon rotation. The helical member 406 includes a structure 410 having coupling feature 418. The coupling feature 418, according to various embodiments, is configured to couple with the tip feature 310 of the inner member 302 in such a manner as to allow torque to transfer from the inner member 302 to the coupling feature 418. This torque will then operate to encourage rotation of the helical member 406. FIG. 3B shows the tip portion 306 of the inner member 302 extending from a distal portion of the outer member 304, according to other embodiments. In FIG. 3B, the distal tip feature 310 (not shown) is coupled or mated with the coupling feature 418 of the implantable lead 14. In this configuration, the stylet 300 can be used to deliver torque to the lead feature by rotating the inner member 302.

According to various embodiments, the inner member 302 is configured to have a torsional stiffness sufficient to deliver a torque input at the proximal end, along its length to the distal end to the anchoring mechanism (e.g., fixation helix) 24, with less than 360 degrees rotation (i.e., twisting) along the length of the inner member 302 (i.e., between the proximal end and the distal end). In particular, according to various embodiments, the inner member 302 has a torsional stiffness sufficient to deliver a torque to the fixation helix, with less than 360 degrees rotation along its length, in an amount in the range between about 10 and about 250 micronewton-meters. In other embodiments, the inner member 302 has a torsional stiffness sufficient to deliver a torque to the fixation helix with less than 360 degrees rotation along its length, in an amount in the range between about 20 and about 100 micronewton-meters. In further embodiments, the inner member 302 has a torsional stiffness sufficient to deliver a torque to the fixation helix, with less than 360 degrees rotation along its length, in an amount in the range between about 30 and about 80 micronewton-meters. In further embodiments, the inner member 302 has a torsional stiffness sufficient to deliver a torque to the fixation helix, with less than 360 degrees rotation along its length, in an amount of at least about 40 micronewton-meters. According to various embodiments, the inner member 302 has sufficient torsional stiffness to deliver a torque to the fixation helix, with less than 24 degrees or rotation along its length, in any of the various amounts set forth above.

Figure 4A:
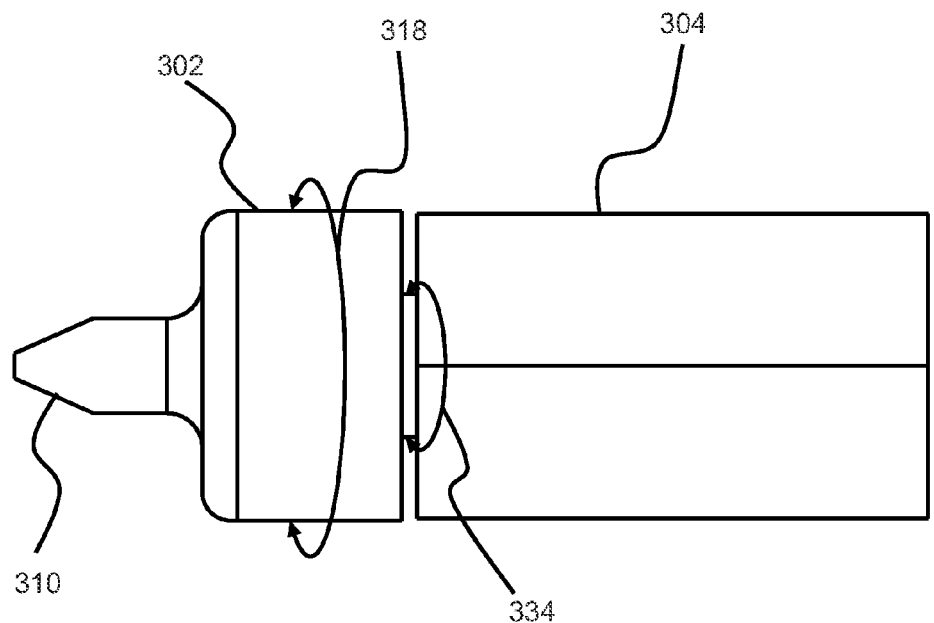
FIG. 4A is a front view of a tip portion attached to a distal end of a first elongate member and a proximal end of a first elongate member enclosed within a second elongate member.
Figure 4B:
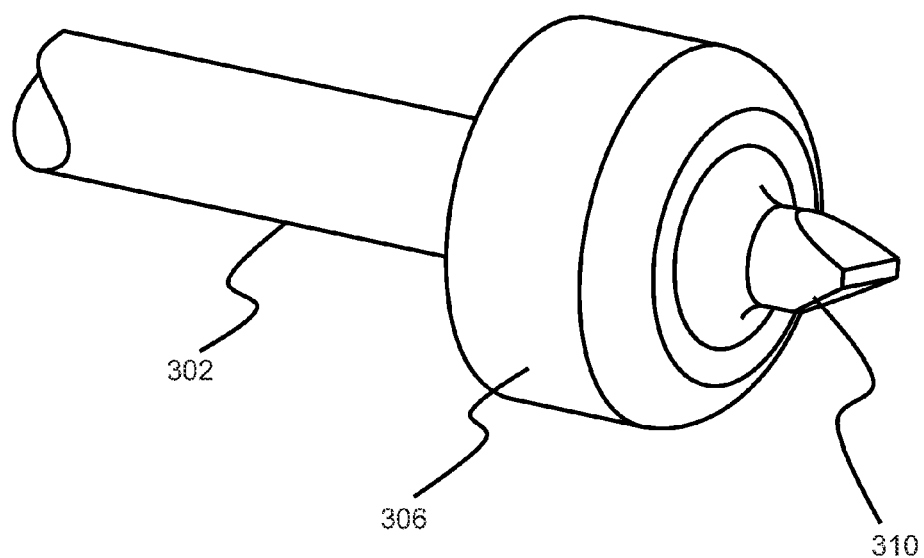
FIG. 4B is a perspective view of a tip portion with a distal end portion and a proximal end portion of a first elongate member.

FIGS. 4A and 4B show further embodiments of a stylet 300. As shown, the distal end portion 306 of the inner member 302 has a diameter larger than an inner diameter of the outer member 304. By having an enlarged diameter, the end portion 306 is prevented from moving longitudinally into the lumen of the outer member 304. In this manner, the inner member 302 is restricted from moving longitudinally with respect to the outer member 304, but remains free to rotate with respect to the outer member 304.

In embodiments of a stylet 300 including an actuating mechanism 326 (as shown, for example, in FIG. 2A), the mechanism can be operated to provide relative longitudinal and/or rotational movement between the inner member 302 and the outer member 304. In various embodiments, the mechanism 326 is configured to advance the inner member 302 with respect to the outer member 304, so as to engage with the lead 14. The actuating mechanism 326 can be configured to actuate and move the inner member 302 back and forth within the lumen 316 of the outer member 304, for example, toward the coupling feature 418 of the lead 14. The actuating mechanism 326 can further be configured to retract the inner member 302 back into the lumen 316 after implant of the lead 14 at the desired implant location. In some embodiments, the actuating mechanism 326 is coupled at the proximal end portion of the outer member 304. In other embodiments, the actuating mechanism 326 is operatively coupled to the inner member 302. In various embodiments, the actuating mechanism 326 can be a handle or a knob wherein rotating the handle or the knob can cause the inner member 302 to rotate and engage with the coupling feature 418 of the lead 14. In some embodiments, the actuating mechanism 326 can be a push button or a piston type arrangement that allows the movement of the inner member 302 forward and backward in order to engage with the lead 14.

During use, the stylet 300 can be inserted into the longitudinally extending lumen of the lead 14. The stylet 300 can be inserted such that the distal tip feature 310 engages the coupling feature 418 at or near a distal end of the lead 14. Upon insertion into the lead 14, the outer member 304 of the stylet 300 imparts (wholly or partially) its predetermined shape onto the flexible lead body, such that the lead 14 may be effectively advanced through the patient's vasculature and directed to a desired implant location or site. For example, in some embodiments, the outer member 304 imparts a J-shape upon the lead 14. The J-shape of the outer member 304 of the medical stylet 300 allows the lead 14 to be placed in the right atrium 26 of the heart 16. Upon reaching the desired implant location near or in the patient's heart, the user (e.g., a physician) imparts a torque upon the inner member 302. This torque is then transferred by the distal tip feature 310 from the inner member 302 to coupling feature 418 on the lead. This torque causes rotation of the helical component, which then advances into and engages the tissue in or near the heart.

Figure 5:
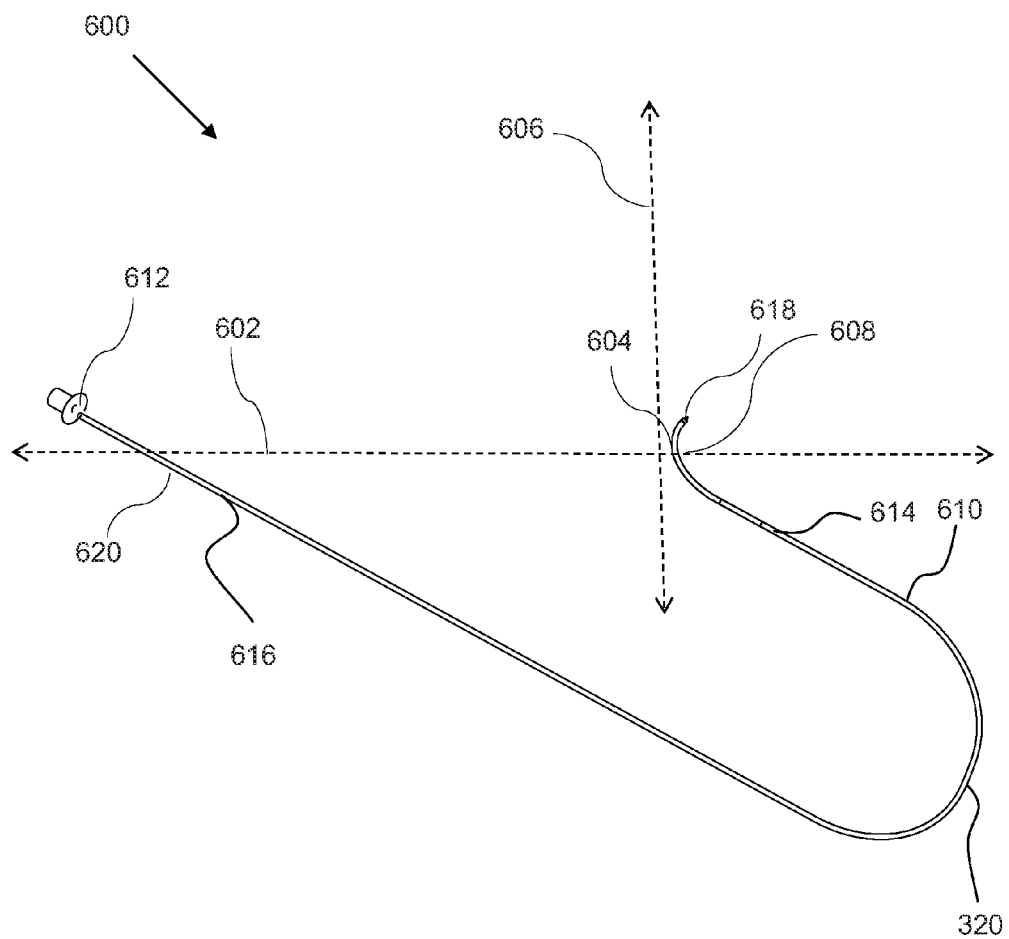
FIG. 5 is a perspective view of a J-shaped stylet placing a lead in an atrium of a heart, according to various embodiments.

FIG. 5 is a perspective view of a compound-shaped medical stylet 600 for imparting a shape to the lead 14 and for delivering torque to a distal anchoring mechanism of the lead 14. In an embodiment, the compound shaped medical stylet 600 can be configured to have more than one curve to provide a compound shape to the lead 14. As shown in FIG. 5, the compound shaped medical stylet 600, according to various embodiments, includes an inner member 608, an outer member 610, and an actuating mechanism 612. The inner member 608 can be similar to the inner member 302 in structure and function. The outer member 610 can be similar to the outer member 304 in structure and function.

The actuating mechanism 612 can be similar to the actuating mechanism 326 in structure and function. The inner member 608 can include a distal end portion 618 and a proximal end portion 620. The outer member 610 can include a distal end portion 614 and a proximal end portion 616.

In various embodiments, the compound shaped medical stylet 600 can be configured so that the outer member 610, the proximal end portion 620, and the actuating mechanism 612 lie in a first plane 602. The distal end portion 618 of the first elongate member 608 can be configured to lie in a second plane 606 that is different from the first plane 602. In some embodiments, the compound-shaped medical stylet 600 is configured so that the outer member 610 defines a curve shape 604 in the plane 606. In various embodiments, the outer member 610 of the stylet 600 is configured to have a pre-defined shape, wherein the pre-defined shape can be a multi-planar shape. In other embodiments, the medical stylet 600 is configured and shaped to be defined along more than two planes so as to provide a multi-planar shape to the compound-shaped medical stylet 600.

Figure 6:
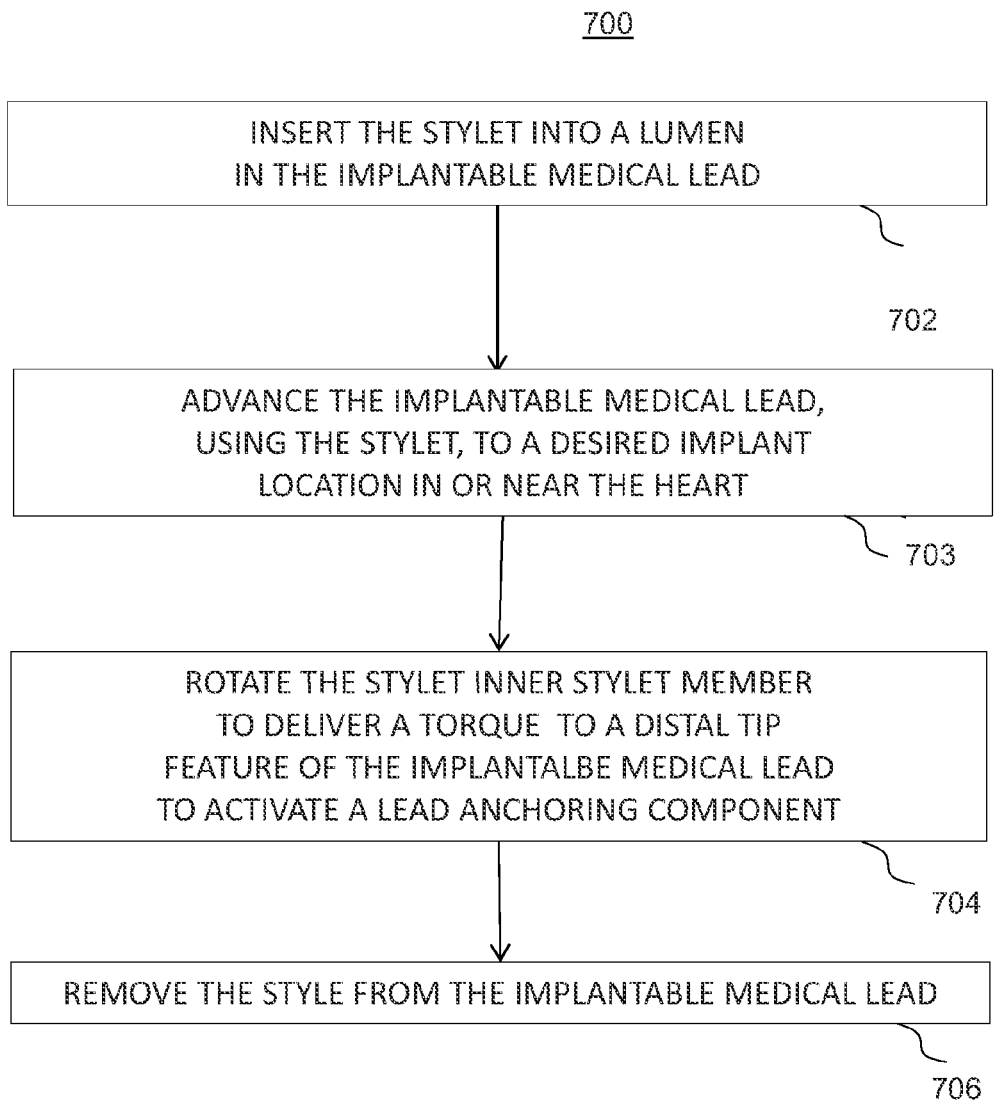
FIG. 6 is a flowchart illustrating a method of placing of a lead in the heart using a stylet.

FIG. 6 is a flowchart illustrating a method 700 of placing the lead 14 in the heart 16 using a medical stylet 300 or 600. The method 700 can include inserting the medical stylet that can be similar to the medical stylet 300 or the medical stylet 600 into the lumen 22 defined by the lead 14 in order to provide the desired shape to the lead 14 as illustrated at step 702. The medical stylet 300 or the medical stylet 600 can be configured to include a first elongate member and a second elongate member for at least partially enclosing the first elongate member; the second elongate member can be configured for providing a shape to the lead 14 in accordance with an anatomical passageway.

The medical stylet can be similar to the medical stylet 300 or the compound shaped medical stylet 600. The second elongate member such as the second elongate member 304 of the stylet such as for example, the medical stylet 300 can be a pre-shaped member that can be configured to allow a shape to be provided to the lead 14, in accordance with the anatomical passageway. The method 700 can further include rotating the medical stylet 300 to cause the first elongate member similar to the first elongate member 302 to engage with the lead 14 to provide torque externally at step 704. In an embodiment, rotating the medical stylet 300 can cause the tip portion 310 of the first elongate member 302 to engage with the lead 14 to externally provide torque to the lead 14. The tip portion 310 of the first elongate member 302 can be configured in different shapes, in accordance with the coupler 356 used in the lead 14. The method 700 can further include guiding the medical stylet 300 along the anatomical passageway to cause the placement of the lead 14 at step 706. The method 700 can include retracting the medical stylet 300 after placing the lead 14 at the anatomical location.

I claim:

1. A medical stylet for use in delivering and anchoring an implantable medical lead to a desired location near or in a patient's heart, the medical stylet comprising:
an inner member, having a distal end portion and a proximal end portion, wherein the distal end portion includes a tip feature, the tip feature configured to rotationally engage a coupling feature at or near a distal end of the implantable medical lead, the coupling feature rotationally coupled to an anchoring mechanism including a fixation feature; and
an outer member defining a lumen along its length, the lumen configured to accept and allow rotation of at least a portion of inner member, the outer member having a predetermined shape and having sufficient stiffness to impart the shape upon the lead, the shape selected to assist in delivery of the lead to the desired implant location;
wherein the inner member has sufficient torsional stiffness to transmit a torque from the proximal end portion to the coupling feature, so as to rotate the anchoring mechanism; and the distal end portion of the inner member has a diameter larger than a diameter of the outer member lumen.

2. The medical stylet of claim 1, further comprising an actuating mechanism and wherein the proximal end portion of the inner member is configured to be rotated by the actuating mechanism.

3. The medical stylet of claim 2, wherein the tip feature is configured to be manipulated by the actuating mechanism to engage with the coupling feature of the implantable medical lead.

4. The medical stylet of claim 1, wherein the inner member is made from at least one of steel, titanium, nickel, and a polymer.

5. The medical stylet of claim 1, wherein the tip feature of the inner member defines a non-circular shape.

6. The medical stylet of claim 1, wherein the predetermined shape of the outer member is a J-shape and the desired location in an atrium of the heart.

7. The medical stylet of claim 1, wherein the predetermined shape of the outer member is an L-shape and the desired location is a His bundle of the heart.

8. The medical stylet of claim 1, wherein the predetermined shape is a multi-planar shape.

9. The medical stylet of claim 1, wherein the outer member is made from at least one of a stainless steel and a nickel-cobalt alloy.

10. The medical stylet of claim 1, wherein the inner member has a torsional stiffness sufficient to deliver a torque to the coupling feature, with less than 360 degrees rotation along its length, in an amount between about 20 and about 100 micronewton-meters.

11. A cardiac lead assembly comprising:
an implantable medical lead including a lead body having a lead proximal end and a lead distal end and a lead lumen extending therethrough, the lead further including an anchoring mechanism disposed at or near the lead distal end, the anchoring mechanism having a coupling feature and a fixation feature;
a stylet for use in guiding the implantable lead to a desired implant site, the stylet comprising:
an inner member, having a distal end portion and a proximal end portion, wherein the distal end portion includes a tip feature, the tip feature configured to rotationally engage the coupling feature at or near the distal end of the implantable medical lead; and
an outer member defining a stylet lumen along its length, the stylet lumen configured to accept and allow rotation of at least a portion of inner member, the outer member having a predetermined shape and having sufficient stiffness to at least partially impart the shape upon the lead, the shape selected to assist in delivery of the desired implant site;
wherein the inner member has sufficient torsional stiffness to transmit a torque from the proximal end portion to the coupling feature, so as to rotate the anchoring mechanism; and the distal end portion of the inner member has a diameter larger than a diameter of the stylet lumen.

12. The cardiac lead assembly of claim 11, wherein the inner member is made from at least one of steel, titanium, nickel, and a polymer.

13. The cardiac lead assembly of claim 11, wherein the tip feature of the inner member defines a non-circular shape.

14. The cardiac lead assembly of claim 11, wherein the anchoring mechanism includes a helix configured for engaging and anchoring with tissue in or near a patient's heart.

15. The cardiac lead assembly of claim 11, wherein the predetermined shape is a multi-planar shape.

16. The cardiac lead assembly of claim 11, wherein the outer member is made from at least one of a stainless steel and a nickel-cobalt alloy.

17. The cardiac lead assembly of claim 11, wherein the inner member has a torsional stiffness sufficient to deliver a torque to the coupling feature, with less than 360 degrees rotation along its length, in an amount between about 20 and about 100 micronewton-meters.

18. The cardiac lead assembly of claim 11, wherein the fixation feature is a fixation helix.

* * * * *